(12) United States Patent
Wood et al.

(10) Patent No.: US 7,429,276 B2
(45) Date of Patent: Sep. 30, 2008

(54) COMPOSITION FOR COLORING OF KERATIN FIBERS

(75) Inventors: Jonathan Wood, Weinheim (DE); Bernd Nöcker, Tokyo (JP); Iijima Makoto, Yachiyo (JP)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 145 days.

(21) Appl. No.: 11/380,469

(22) Filed: Apr. 27, 2006

(65) Prior Publication Data

US 2006/0248661 A1 Nov. 9, 2006

(30) Foreign Application Priority Data

May 3, 2005 (EP) ................... 05009680

(51) Int. Cl.
*A61Q 5/10* (2006.01)
(52) U.S. Cl. ................. 8/405; 8/406; 8/410; 8/411; 8/415; 8/435; 8/455; 8/463; 8/552; 8/581; 132/202; 132/208
(58) Field of Classification Search .......... 8/405, 8/406, 410, 411, 415, 435, 455, 463, 552, 8/581; 132/202, 208
See application file for complete search history.

(56) References Cited

U.S. PATENT DOCUMENTS

| 5,006,127 | A * | 4/1991 | Tennigkeit et al. | ............. 8/406 |
| 5,618,525 | A * | 4/1997 | Bunning | ............. 424/70.122 |
| 6,537,328 | B1 * | 3/2003 | Lang et al. | ............. 8/405 |
| 2004/0237217 | A1 * | 12/2004 | Desenne et al. | ............. 8/405 |

OTHER PUBLICATIONS

Eisa Elilo/ Primary Examiner, A.U. 1796.*

* cited by examiner

*Primary Examiner*—Eisa B Elhilo

(57) ABSTRACT

The present invention concerns a composition for the dyeing keratin fibers especially human hair on the basis of an oxidation dyestuff precursor system reacting with peroxide and comprising additionally anionic direct dyes which provides long-lasting, intensive, vibrant colors. Hair dyeing composition of the present invention comprises at least one oxidation dyestuff precursor reacting with peroxide, optionally at least one coupling agent and at least one acidic direct dye. The compositions of the present invention do not comprise any cationic dyes.

12 Claims, No Drawings

COMPOSITION FOR COLORING OF KERATIN FIBERS

FIELD OF THE INVENTION

Present invention relates to a composition for the dyeing keratin fibers especially human hair on the basis of an oxidation dyestuff precursor system reacting with peroxide and comprising additionally anionic direct dyes which produces long-lasting, intensive, vibrant colors.

BACKGROUND OF THE INVENTION

Hair dyeing compositions based on oxidative dyes has been known for decades. They are believed to be producing intensive, long lasting, stable hair colors. However, their shortcoming is known in achieving wide range of color assortment. In order to achieve a full hair color assortment, usually additional dyes known as direct dyes are used in addition to oxidative dyes. Those direct dyes are as a rule up until now of cationic and nonionic character. Recently, It has been shown that anionic direct dyes alone also achieves long lasting intensive colors, especially when used in acidic pH ranges (EP 1022044A1). Additionally, attempts have been made to use anionic direct dyes alone in alkaline pH ranges in the presence of oxidizing agents (Unpublished European Patent application of the applicant, Application no: 04 001 799.8). The colors so achieved is intensive but their durability is not always found to be satisfying.

In a recent study of the applicant, it has been shown that an oxidative dyeing composition comprising anionic and cationic direct dyes in addition to oxidative dyestuffs precursors and optionally coupling agents produces long lasting intensive hair colors (European Patent Application Numbers 04 012 176.6, 04 012 177.4, 04 012 178.2). However, because of economical reasons the study has been set forth to find out more economical hair dyeing composition without loosing its performance.

Vibrancy of a hair color is one of the most important criteria to judge its beautifulness. Colors achieved only with oxidative dyes often lack vibrancy especially in red and reddish shades. It is further need of the consumers that especially with red and reddish shades more vibrant colors are provided and the vibrancy of the color so achieved is also long lasting, i.e. after repeatedly shampooing or by the environmental influences such as sun light and sweating, vibrancy of the color is kept as high as possible.

SUMMARY OF THE INVENTION

The present invention starts from the above described problems and provides hair dyeing compositions for achieving intensive, long lasting and vibrant colors. It is especially the object of the current invention to provide hair dying composition to achieve intensive, long lasting and vibrant colors in red and reddish shades.

It is further object of the present invention the use of the hair dyeing compositions according to the invention to achieve intensive, long lasting and vibrant colors.

It is still further object of the present invention that use of hair dyeing compositions to achieve intensive, long lasting vibrant red and reddish colors.

By the term reddish color it is meant that a red touch (shimmer) is achieved on top of a base hair color. The terms coloring and dyeing refer to the same throughout the description.

DETAILED DESCRIPTION OF THE INVENTION

The problem is solved with a hair dyeing composition comprising at least one oxidation dyestuff precursor reacting with peroxide, optionally at least one coupling agent and at least one acidic direct dye. The compositions of the present invention do not comprise cationic dyes. Although cationic dyes are not needed to solve the above described problems and accordingly excluded from the scope of the present inventions, addition of very small quantities should principally be allowed when needed because of any reason. In any case the quantity of the cationic direct dye within the scope of the current invention should never exceed 10% of the total anionic direct dye concentration by weight, excluding oxidizing agent.

Suitable oxidative dye precursors are of those parasol derivatives are such as 1-hydroxyethyl-4,5-diaminopyrazole, 3,4-daimio-5-hydroxypyrazole, 3,5-diaminopyrazole, 3,5-daimio parasol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methyl ethyl-4,5-diaminopyrazole, 1-phenyl methyl-4,5-diaminopyrazole, 1-methyl-4,5-diaminopyrazole, 1-(4-methyl phenyl)methyl-4,5-diaminopyrazole, 1-methyl-3-phenyl-4,5-diaminopyrazole and the water-soluble salts. Further suitable are tetraaminopyrimidines are in particular 2,4,5,6-tetraaminopyrimidine and the lower alkyl derivatives thereof; suitable triaminohydroxypyrimidines are, for example 4-hydroxyl-2,5,6-triaminopyrimidine, 2-hydroxyl-4,5,6-triaminopyrimidine and 5-hydroxyl-2,4,6-triaminopyrimidine; suitable mono- and daimio dihydroxypyrimidines are, for example, 2,6-dihydroxy-4,5-diaminopyrimidine, 2,4-daimio-6-hydroxy-pyrimidine or 4,6-dihydroxy-2,5-diaminopyrimidine or the water-soluble salts thereof, aminophenol derivatives such as 4-aminophenol, 4-amino-3-methyl phenol, 2-chloral-4-aminophenol, 2,6-dichloride-4-aminophenol, 2,4-daimio-phenol, 2,6-dayroom-4-aminophenol and/or 2-aminophenol and water-soluble salts thereof, furthermore, phenylenedimanine derivatives such as 2,5-daimio-toluene, 2-n-propel or 2-ethyl-p-phenylene-diamine, 2,6-dimethyl-p-phenylenediamine, 2-(2,5-diaminophenyl) ethanol, 1-amino-4-bus-(2'-hydroxyl-ethyl)amino benzene, 2-(2-hydroxyethyl amino)-5-amino toluene, 4,4'-diaminodiphenylamine, 4-amino diphenylamine, 2-amino-5-N,N-diethyl amino toluene, 4-amino-N-ethyl-N-isopropyl aniline, 2-chloro-p-phenylenediamine, 1-β-hydroxyethyl-2,5-daimio-4-chlorobenzene, 1-β-hydroxyethyl-2,5-daimio-4-methyl benzene, 2-methoxy-p-phenylenediamine, N,N-diethyl-p-phenylenediamine, 1-amino-4-β-methoxyethyl amino benzene, 1-diethyl-amino-4-amino benzene, 1-hydroxyl-2,5-daimio-4-methyl benzene, 1-hydroxymethyl-2,5-diaminobenzene, 1.3-diethyl-2,5-diaminobenzene, 1,4-daimio isopropyl benzene and/or 1-amino-4-β-hydroxypropyl amino benzene or the water-soluble salts thereof.

Among those, 2,4,5,6-tetraminopyrimidine, 4-aminophenol, 4-amino-3-methyl phenol, 2,5-daimio-toluene and 2-(2,5-diaminophenyl)ethanol are the most preferred oxidative dye precursors.

The total concentration of the oxidation dyestuff precursors and/or their water soluble salts customarily ranges between about 0.01% and 5%, preferably 0.05% and 4%, in particular 0.1% to 3% by weight, calculated to the total hair dyeing composition (excluding the oxidation agent), whereby these figures are always related to the proportion of free base.

The composition according to the invention preferably comprises at least one coupling substance, which can be selected from resorcinol, 2-methyl resorcinol, 4-amino-2-methyl phenol, 4-chlororesorcinol, 2-amino-4-chloroprene, 5-amino-4-metonym-2-methyl phenol, 3-amino-phenol, 1-methyl-2-hydroxyl-4-amino benzene, 3-N,N-diethyl aminophenol, 2,6-dihydroxy-3,5-dimethoxypyridine, 5-amino-3-methyl phenol, 6-amino-3-methyl phenol, 3-amino-2-methylamine-6-methoxypyridine, 2-amino-3-hydroxyl-pyridine, 2-diethyl-amino-5-amino pyridine, 2,6-diaminopyridine, 1,3-daimio-benzene, 1-amino-3-(2'-hydroxyethylamino)benzene, 1-amino-3-[bus(2'-hydroxylethyl)amino]benzene, α-naphtha, 4,6-dichlororesorcinol, 1,3-daimio-toluene, 1-hydroxyl naphthalene, 4-hydroxyl-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxyl-2-methyl naphthalene, 4-hydroxyl-1,2-methyldioxy benzene, 2,4-daimio-3-chloroprene, 2,6-dihydroxyethylamino toluene, 5-amino-2-methoxyphenol and/or 1-metonym-2-amino-4-(2'-hydroxyethyl amino)benzene or the water-soluble salts thereof.

The most preferred coupling agents are 2,6-dihydroxyethylamino toluene, 2-methyl resorcinol, 4-amino-2-methyl phenol and α-Naphtali.

In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

The weight proportion of the developing substances to the coupling substances in general ranges between about 1:8 to 8:1, preferably about 1:5 to 5:1, in particular 1:2 to 2:1 and most preferably 1:1.

According to the invention the suitable anionic direct dyes are:

Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10. The most preferred anionic dyes are Acid Red 52, Acid Violet 2, Acid Red 33, Acid Orange 4 and Acid Yellow 10.

According to the invention, coloring composition comprises anionic dyes at a total concentration of 0.01 to 7.5%, preferably 0.02 to 6%, more preferably 0.05 to 5%, in particular 0.1 to 4%, most preferably 0.2 to 3% and most particularly 0.5 to 3% by weight, calculated to total composition excluding the oxidizing agent.

Use of these compositions on the basis of a customary carrier provides very expressive, intensive, long-lasting vibrant hair colorations.

Additionally, the coloring compositions of the present invention may comprise neutral dyes (HC dyes), so called nitro dyes for shading purposes. Concentration of those can typically be in the range from 0.01 to 2.5%, preferably 0.1 to 2% by weight calculated to total composition, excluding the oxidizing agent.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloral-4-nitro phenol, pyramid acid, 1,2-Daimio-4-nitrobenzol, 1,4-Daimio-2-nitrobenzol, 3-Nitro-4-aminophenol, 1-Hydroxyl-2-amino-3-nitrobenzol and 2-hydroxyethylpicramic acid.

Plant dyestuffs can also be used alone or in combination with synthetic direct-acting dyestuffs, for example henna (red or black), alkanet root, lactic acid, indigo, logwood powder, madder root and rhubarb powder, etc.

Hair dyeing composition of the present invention may comprise an organopolysiloxane wherein at least one siliceous atom is linked to an alkaline group having a heteroatom, in particular a nitrogen atom, with a poly-(N-acryl alkyleneimine) units of the formula

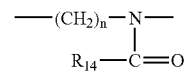

wherein n is a number from 1 to 5 and $R_{14}$ is hydrogen, a $C_1$-$C_{12}$-alkyl or cyclically, a alkyl or aryl group.

Preferred organopolysiloxane polymers are those of the type disclosed in EP-A 640 643, in particular optionally quaternized amino alkyl, in particular aminopropyl diethyl polysiloxane/polyethyl oxazoline copolymers of the formula

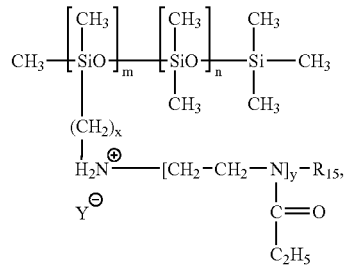

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair coloring compositions according to the invention ranges from 0.05% to 5%, preferably 0.1% to 2.5%, in particular 0.5% to 1.5% by weight, calculated to the total composition.

Another preferred compound in the coloring composition may be included is that of creamed type of compounds according to general formula

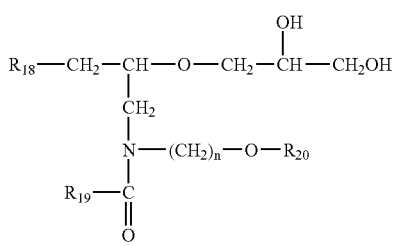

where $R_{18}$ and $R_{19}$ are independent from each other alkyl- or. alchemy group mitt 10 to 22 carbon atoms, $R_{20}$ is methyl, ethyl, n-propel or isopropyl group and n is a number between 1 to 6, preferably 2 or 3. The concentration of creamed type of compound in coloring compositions of the present invention can be in the range of 0.01 to 2 and especially 0.01 to 1% by weight calculated to the total composition.

The compositions of the present invention may comprise one or more ubiquinone of the formula.

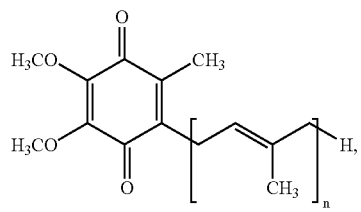

wherein n is a number from 1 to 10. Concentration of ubichinones in the compositions of the present invention can vary between 0.001% and 10% by weight, calculated to the total composition excluding oxidizing agent.

Coloring composition of the present invention may comprise compounds for accelerating (catalysts) the oxidative dyeing keratin fibers such as iodine salts i.e. potassium or sodium iodide and/or dihydroxy acetone.

The hair dyeing compositions according to the invention can comprise the basic substances and additives customarily found in such compositions, conditioning agents, etc., known as state of the art and described, for example, in the monograph of K. Schrader, "Groundage und Retexture der Kosmetika", 2nd Ed. (Hüthigh Buch Verlag, Heidelberg, 1989), pp. 782 to 815. They can be prepared as solutions, creams, gels or also in the form of aerosol products; suitable carrier material compositions are known as state of the art.

Hair dyeing is carried out within the scope of the present invention wherein that the composition according the present invention comprising at least one oxidation dyestuff precursor and at least one anionic direct dye, optionally at least one coupling agent is mixed with a composition comprising an oxidizing agent, preferably hydrogen peroxide, prior to application and then applied onto hair. Processing time is usually 15 to 45 min at ambient temperature or at a temperature between 30 and 45° C. After the processing time lapsed the hair is rinsed off. The preferred oxidizing agent is hydrogen peroxide, at a concentration of 2 to 12% by weight. However, the use of other peroxides such as urea peroxide and melamine peroxide is also possible.

As an alternative to peroxide oxidation, it is also possible to achieve the oxidation by air, for example, by applying onto the hair a composition comprising an oxidation dyestuff precursor as aerosol foam and leaving to process for about 15 to 20 minutes.

The pH-value of the ready-to-use hair dyeing composition, i.e. after mixing with peroxide, can be between 5 and 12, preferably 6-11, more preferably 6.8 to 10.

Composition of the present invention is provided to consumers in the form of a kit comprising separately packed dyeing composition (A) comprising at least one oxidative dye precursor and at least one anionic direct dye and optionally at least one coupling agent and an oxidizing composition (B) comprising at least one oxidizing agent, preferably hydrogen peroxide.

The following examples are to illustrate the invention without limiting it.

Carrier

| | | |
|---|---|---|
| Stearyl alcohol | 8.0 | (% by wt.) |
| Coco fatty acid monoethanolamide | 4.5 | |
| 1,2-Propanediol mono/distearate | 1.3 | |
| Coco fatty alcohol polyglycolether | 4.0 | |
| Sodium lauryl sulfate | 1.0 | |
| Oleic acid | 2.0 | |
| 1,2-Propanediol | 1.5 | |
| Na-EDTA | 0.5 | |
| Sodium sulfite | 1.0 | |
| Protein hydrolyzate | 0.5 | |
| Ceramide according to formula where $R_{18}$ and $R_{19}$ are C16 and $R_{20}$ is ethyl | 0.2 | |
| Ascorbic acid | 0.2 | |
| Organopolisiloxane according to EP640643 Compound A-1 | 0.3 | |
| Perfume | 0.4 | |
| Ubichinone 10 | 0.1 | |
| Ammonia, 25% | 1.0 | |
| Ammonium chloride | 0.5 | |
| Panthenol | 0.8 | |
| Water | ad 100.00 | |

The dyestuff combinations oxidative and ("or" only with oxidative dyes for comparative purposes) anionic dyes were incorporated into this carrier, whereby the water content was reduced accordingly.

The colorations were carried out on wool patches, strands of bleached human hair and natural human hair at a color level of 8 by application of a 1:1 mixture of an emulsion comprising the dyestuffs as given in the examples below and a 6% hydrogen peroxide solution (pH-value of the mixture: 9.8) with 30 minutes processing at 40° C., subsequent rinsing and drying.

Hair dyeing compositions with the following oxidative dye precursor and coupling agent and anionic direct dye content were prepared.

TABLE I

Examples 1 to 4

| | Examples | | | |
|---|---|---|---|---|
| | I | II | III | IV |
| 2,4,5,6-tetraaminopyrimidine | 1.20 | 1.20 | 1.20 | 1.20 |
| 2-methyl resorcinol | 0.62 | 0.62 | 0.62 | 0.62 |
| Acid Red 52, | — | 0.50 | — | — |
| Acid Orange 4 | — | — | 0.50 | — |
| Acid Yellow 10. | — | — | — | 0.50 |
| Hair colour | Reddish-copper | Reddish-copper | Vibrant-copper | Copper |
| L1 | 30.81 | 30.92 | 35.20 | 35.55 |
| a | 35.62 | 42.51 | 41.24 | 38.20 |
| b | 18.70 | 13.96 | 25.88 | 25.73 |
| C1 (Vibrancy) | 40.23 | 44.74 | 48.69 | 46.06 |

Examples II to IV are according to the invention and example I is for comparative purposes. The above L, a and b results were obtained on a bleached hair tress.

L, a and b values were measured optically using a laboratory equipment purchased from Minolta.

Vibrancy of hair color (C value) is calculated from a and b values measured, according to the following equation:

$$\text{Vibrancy}(C) = \text{Squareroot}(a^2 + b^2)$$

From the above results it is clear that dyeing compositions (Examples II to IV) according to the invention produces more vibrant colors.

In order show color fastness (durability) against washing, all colored strands were washed 10 times under usual hair wash conditions with a commercial shampoo composition designed for colored hair of the trade mark Goldwell, and color of the tresses (L, a and b values) were measured before and after shampooing optically with a laboratory equipment. Color differences were calculated with the well known equation to obtain ΔE values and color intensity differences (ΔL) were obtained from measured L values. Additionally from a and b values C values were calculated with the equating given above. The results are presented in the Table II below.

TABLE II

Results of the durability test

| Example | L2 | ΔE | C2 |
|---|---|---|---|
| I | 39.7 | 10.5 | 35.1 |
| II | 36.5 | 6.6 | 44.7 |
| III | 38.9 | 6.2 | 48.7 |
| IV | 41.8 | 6.1 | 46.1 |

L1 (See table 1) stands for the intensity of the color measured before the washing test and L2 is the same value measured after washing the strands 10 times with shampoo. C1 (see table 1) and C2 are the values obtained before and after washing, respectively. ΔE value is obtained from the L, a and b values measured before and after washing. From the L1 and L2 values it is clear that addition of acidic dyes resulted in more stable coloration against washing. This is furthermore expressed with ΔE values as the color difference. C2 value for example I was obviously changed after washing and for examples II to IV (inventive compositions) remained unchanged. Upon macroscopic evaluation by the hair dressers, the examples 2 to 4 are judged to be more vibrant than example 1 both before and after washing. The difference is increased especially after washing.

TABLE III

Examples 5 to 7

| | Examples | | |
|---|---|---|---|
| | V | VI | VII |
| 2,4,5,6-tetraaminopyrimidine | 1.20 | 1.20 | 1.20 |
| 2-methyl resorcinol | 0.31 | 0.31 | 0.31 |
| 2,6-dihydroxyethylamino toluene | 0.52 | 0.52 | 0.52 |
| Acid Red 52, | — | 0.50 | — |
| Acid Orange 4 | — | — | 0.50 |
| Hair colour | Copper red | Vibrant red | Copper red |
| L1 | 32.92 | 31.28 | 34.81 |
| a | 43.06 | 46.23 | 44.14 |
| b | 21.32 | 16.75 | 26.25 |
| C1 | 48.1 | 49.2 | 51.36 |

Example V is comparative and Examples VI and VII are according to the invention.

The measurements and calculations and durability tests were carried out as described above for examples I to IV.

From the above results it should be concluded that the inventive compositions (Examples VI and VII) produced vibrant colors.

TABLE IV

Results of the durability test

| Example | L2 | ΔE | C2 |
|---|---|---|---|
| V | 42.1 | 9.0 | 43.2 |
| VI | 36.5 | 6.5 | 50.5 |
| VII | 39.3 | 4.5 | 51.1 |

From the results it is clear, same as in the examples 1 to 4, the compositions according to present invention produced more wash stable, and vibrant hair colors. The vibrancy was observed to be stable even when hair is shampooed.

TABLE V

Examples 8 to 10

| | Examples | | |
|---|---|---|---|
| | VIII | IX | X |
| p-aminophenol | 0.28 | 0.28 | 0.28 |
| p-amino-o-cresol | 0.30 | 0.30 | 0.30 |
| Acid Red 52, | — | 0.50 | — |
| Acid Orange 4 | — | — | 0.50 |
| Hair colour | Copper | Red copper | Vibrant copper |
| L1 | 34.88 | 36.05 | 41.58 |
| a | 36.05 | 51.81 | 40.57 |
| b | 29.59 | -1.51 | 39.18 |
| C1 | 46.6 | 51.8 | 56.4 |

Example VIII is comparative and Examples IX and X are according to the invention.

The measurements and calculations and durability tests were carried out as described above for examples I to IV.

It is clear from the above results that more vibrant colors were obtained with inventive compositions (Example IX and X) compared to the comparative composition comprising only oxidative dyes (Example VIII).

TABLE VI

Results of the durability test

| Example | L2 | ΔE | C2 |
|---|---|---|---|
| I | 57.9 | 14.1 | 42.6 |
| II | 46.9 | 6.3 | 54.6 |
| III | 49.8 | 9.0 | 56.5 |

From the results it is clear, same as in the previous examples, the compositions according to present invention produced more wash stable, and vibrant hair colors. The vibrancy was observed to be stable even when hair is shampooed.

Similar results were obtained with the examples below wherein the anionic dyestuff concentration was reduced.

| | Examples | | | | |
|---|---|---|---|---|---|
| | XI | XII | XIII | XIV | XV |
| 2,4,5,6-tetraaminopyrimidine | 1.20 | 1.20 | — | 1.20 | 1.20 |
| 2-methyl resorcinol | 0.31 | 0.31 | — | 0.31 | 0.31 |
| 2,6-dihydroxyethylamino toluene | — | 0.52 | — | 0.52 | 0.52 |
| p-aminophenol | — | — | 0.28 | — | — |
| p-amino-o-cresol | — | — | 0.30 | — | — |
| Acid Red 52, | 0.10 | — | — | — | — |
| Acid Orange 4 | — | 0.15 | — | 0.05 | — |
| Acid Yellow 10. | — | — | 0.25 | — | 0.15 |

The invention claimed is:

1. A process for colouring hair comprising the steps of:
providing a first composition comprising at least one oxidation dye precursor and at least one acidic direct dye selected from Acid Red 52, Acid Violet 2, Acid Orange 4, Acid Red 27 and Acid Yellow 10, with the condition that it does not comprise cationic direct dye,
mixing the first composition with a second composition comprising a hydrogen peroxide to form a third composition, wherein the third composition has a pH between 6.8 and 12, and
applying the third composition onto hair for a period between 15 and 45 minutes at ambient temperature and/or at a temperature between 30 and 45° C.

2. The process according to claim 1 wherein the oxidative dye precursor of the first composition is selected from 2,4,5,6-tetraaminopyrimidine, 4-aminophenol, 4-amino-3-methylphenol, 2,5-daimio-toluene and 2-(2,5-diaminophenyl)ethanol.

3. The process according to claim 1 wherein the first composition comprises additionally at least one coupling agent.

4. The process according to claim 1 wherein the first composition comprises additionally at least one coupling agent selected from 2,6-dihydroxyethylamino toluene, 2-methyl resorcinol, 4-amino-2-methylphenol and α-naphtol.

5. The process according to claim 1 wherein the first composition comprises oxidative dye precursor at a concentration of 0.01 to 5% by weight calculated to total composition, excluding oxidizing agent.

6. The process according to claim 1 wherein the first composition comprises anionic direct dye at a concentration of 0.01 to 7.5% by weight calculated to total composition excluding oxidizing agent.

7. The process according to claim 1 wherein the first composition comprises organosiloxane polymer according to formula

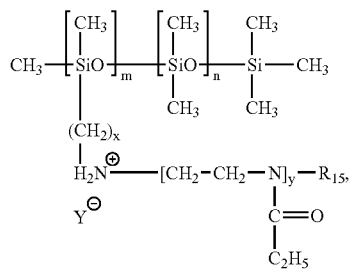

wherein m and n each are numbers from 20 to 10,000, x is a number between 1 and 5, and y is a number from 5 to 30, $R_{15}$ is a $C_1$-$C_{12}$-alkyl or aryl group- and $Y^-$ is an anion.

8. The process according to claim 1 wherein the first composition comprises additionally at least one ceramide type compound according to the formula

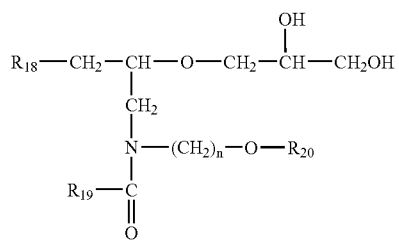

where $R_{18}$ and $R_{19}$ are independent from each other alkyl- or. alkenyl group mit 10 to 22 carbon atoms, $R_{20}$ is methyl, ethyl, n-propyl or isopropyl group and n is a number between 1 to 6.

9. The process according to claim 1 wherein the first composition comprises at least one ubiquinone of the formula

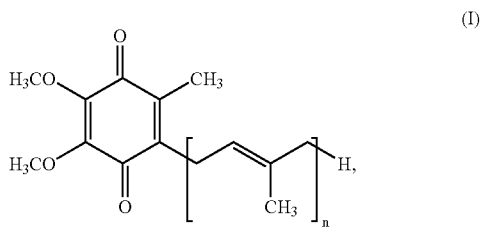

wherein n is a number from 1 to 10.

10. The process according to claim 1 wherein the first composition comprises additionally neutral direct dyes.

11. The process according to claim 1 wherein the first composition comprises additionally potassium or sodium iodide and/or dihydroxyacetone as catalysts.

12. The process according to claim 7, wherein $R_{15}$ is a methyl, ethyl or benzyl group.

* * * * *